United States Patent [19]

Firth

[11] Patent Number: 5,066,305

[45] Date of Patent: Nov. 19, 1991

[54] PROSTHETIC FOOT HAVING A LOW PROFILE CANTILEVER SPRING KEEL

[75] Inventor: David G. Firth, Seattle, Wash.

[73] Assignee: Model & Instrument Development Corporation, Seattle, Wash.

[21] Appl. No.: 262,464

[22] Filed: Oct. 25, 1988

[51] Int. Cl.$^5$ .............................................. A61F 2/66
[52] U.S. Cl. ........................................ 623/55; 623/53
[58] Field of Search ................................. 623/53-56

[56] References Cited

U.S. PATENT DOCUMENTS

| | | | |
|---|---|---|---|
| 598,230 | 2/1898 | Roberts | 623/56 |
| 2,289,154 | 7/1942 | Van Cise | 623/54 X |
| 3,335,428 | 8/1967 | Gajdos . | |
| 3,833,941 | 9/1974 | Wagner . | |
| 3,874,004 | 4/1975 | May . | |
| 3,890,650 | 6/1975 | Prahl | 623/55 |
| 4,091,472 | 5/1978 | Daher et al. . | |
| 4,302,856 | 12/1981 | May . | |
| 4,547,913 | 10/1985 | Phillips | 623/53 X |
| 4,619,661 | 10/1986 | Axelsson | 623/55 |
| 4,645,509 | 2/1987 | Poggi et al. | 623/55 |
| 4,652,266 | 3/1987 | Truesdell | 623/55 |
| 4,865,612 | 9/1989 | Arbogast et al. | 623/55 |

FOREIGN PATENT DOCUMENTS

| | | | |
|---|---|---|---|
| 94444 | 10/1897 | Fed. Rep. of Germany | 623/55 |
| 3309777 | 9/1984 | Fed. Rep. of Germany | 623/54 |
| 1371996 | 10/1974 | United Kingdom | 623/55 |
| 2092451 | 8/1982 | United Kingdom | 623/53 |
| 2187102 | 9/1987 | United Kingdom | 623/55 |
| 8909036 | 10/1989 | World Int. Prop. O. | 623/53 |

OTHER PUBLICATIONS

Carbon Copy II S.A. C.H., Preliminary Fact Sheet and Preliminary Data Sheet.
Copes/Bionic Ankle-Brochure, 1985.
Quantum Brochure by J. E. Hanger & Co. Ltd.

*Primary Examiner*—David J. Isabella
*Assistant Examiner*—David H. Willse
*Attorney, Agent, or Firm*—Christensen, O'Connor, Johnson & Kindness

[57] ABSTRACT

A prosthetic foot (10) includes a viscoelastic cantilever spring keel (12) encased in foamed polymer cover (14) shaped to resemble a human foot. The keel (12) includes an attachment flange (16) for connecting the keel to an upper prosthesis at a location generally corresponding to the location of the ankle joint of a human foot. The keel (12) also includes a forefoot portion in the form of a singular beam (22) cantilevered forwardly and diagonally downwardly from the mounting flange (16). The beam (22) is composed of a primary section (50) extending forwardly from the attachment flange (16) and a forward portion (48) having a significantly lower spring rate and, thus, substantially more compliant than the adjacent portions of the beam primary section (50).

26 Claims, 2 Drawing Sheets

PROSTHETIC FOOT HAVING A LOW PROFILE CANTILEVER SPRING KEEL

TECHNICAL FIELD

The present invention relates to a prosthetic foot, and more particularly to a prosthetic foot utilizing an energy storing, low profile cantilever spring keel attachable to a leg prosthesis at substantially the location of a natural ankle joint.

BACKGROUND OF THE INVENTION

Although prosthetic feet have been in use for many years, not until relatively recently have efforts been made to design the prosthetic feet to dynamically interact with the cyclic loading and unloading of the foot during body movements thereby to more closely simulate natural body movement and gait. To this end, such prostheses typically are configured to store and release energy during normal body movements.

One such type of prosthesis is disclosed by U.S. Pat. No. 4,547,913 which concerns a prosthetic device having an upwardly extending leg portion, a foot portion extending forwardly from the bottom of the leg portion and a heel portion extending rearwardly from the bottom of the leg portion, with all three portions rigidly joined together. The three portions of the prosthesis are composed of elastic, flexible material to absorb strain energy and thereafter release the energy during leg and foot movement. A substantial drawback of the prosthesis disclosed in the '913 patent is that the leg portion of the prosthesis precludes it from serving as only a foot prosthesis. Moreover, the spring rate of the foot portion of the prosthesis appears to vary at a fairly uniform rate along the length thereof. However, to closely simulate normal gait it is desirable that the prosthesis exhibit a relatively low spring rate and thus high compliance during initial footfall followed by a substantially higher spring rate to carry the weight of the amputee without further substantial deflection of the prosthesis to avoid excessive lowering of the hip.

United Kingdom Patent Publication 2,187,102 discloses another type of prosthetic foot having a keel and an underlying leaf spring stiffener located beneath the keel. The keel includes front and rear snubbers at the extremities thereof. During normal ambulation the leaf spring is said to provide the primary path by which ground reaction is transmitted to the keel but at high levels of ground reaction the ends of the leaf spring flex upwardly to contact against the overhead snubbers whereby the ground reaction is transmitted directly to the keel. This construction is said to provide substantial compliance during normal movement, such as walking, while also accommodating the higher loads generated during jumping or similar movements. However, a serious drawback of this type of prosthesis is that when the underlying leaf spring deflects upwardly to bear against the keel snubber, the resistance to further deflection abruptly increases significantly. Moreover, the prosthetic foot is composed of numerous separate components which must be individually manufactured and then fastened together by bolts that may loosen over time.

A further type of prosthetic foot is disclosed in U.S. Pat. No. 4,645,509, which has been assigned to Model And Instrument Development Corporation, of Seattle, Washington, which is also the assignee of the present invention. In the '509 patent, the prosthesis includes a monolithic cantilever keel having an attachment flange for connection to an upper prosthesis, an arched heel portion curving initially downwardly and rearwardly from the attachment flange and then forwardly to join a forefoot portion. The curved heel and the forefoot portion are shaped and dimensioned to have a substantially uniform bending stress distribution and strain energy storage throughout their lengths. A significant drawback of the keel of the '509 patent is that the attachment flange thereof is at a relatively high elevation which is substantially above the location of the ankle joint in a natural foot. Moreover, primarily due to relatively large size of the keel, the prosthetic foot of the '509 patent is relatively heavy, making it tiresome to wear over extended periods or during strenuous activities. Since the prosthetic foot is continually accelerated and decelerated during body movement, it is imperative that the foot be as light in weight as possible.

SUMMARY OF THE INVENTION

The foregoing shortfalls of energy restoring prosthetic feet are addressed by the present invention which provides a prosthetic foot having a "low profile" cantilever spring keel composed of viscoelastic material. The keel is encased within a cover composed of low density resilient but durable material having an exterior shape generally resembling a human foot. The keel is constructed with an attachment flange disposed low enough in the foot to connect the keel to an upper prosthesis at an elevation in the prosthetic foot corresponding to the elevation of an ankle joint of a human foot. The keel also includes an elongate forefoot portion that is cantilevered forwardly and diagonally downward from the attachment flange. The forefoot portion is shaped and dimensioned to flex upwardly and thereby store strain energy during footfall and then with the following footrise release such strain energy to provide lift and thrust to assist the wearer to achieve a natural gait. During footfall, the location of the upwardly directed reaction force acting on the keel forefoot portion shifts rearwardly along the keel so as to progressively decrease the effective beam length and progressively increase the spring rate of the keel. As a result, the keel is capable of withstanding a substantial reaction force relative to the size and weight of the keel.

In another aspect of the present invention, the forefoot portion of the keel is constructed in the form of a singular beam having a forward section and a primary section extending between the forward section and the attachment flange. The forward section of the cantilevered beam has a significantly lower spring rate and thus is substantially more compliant than the adjacent portions of the primary section of the beam.

In a further aspect of the present invention, the primary section of the keel forefoot beam is shaped in the form of a parabolic taper with the bottom surface of the beam being generally planar and the upper surface of the beam having a longitudinal profile to form the thickness of the primary section as a parabolic taper. The particular parabolic taper employed in the keel beam is designed to impart a progressively lower bending stress along the primary section in the rearward direction, i.e., from the forward section to the attachment flange of the keel.

In an additional aspect of the present invention, a substantially rigid, but thin toe plate is enclosed in the cover immediately below the front tip of the keel to increase the structural integrity of the cover and to assist in distributing about a substantial area the downward force imposed on the bottom of the cover by the keel as it is flexed during footfall.

In yet an additional aspect of the present invention, the keel includes a heel ledge extending rearwardly from the mounting flange of the keel in the direction opposite to the forefoot beam. The sides of the heel ledge are tapered in a direction away from the mounting flange. In addition, the underside of the heel ledge is sloped upwardly in the rearward direction to provide more room for the resilient, lighter density cover material at the heel strike.

In still another aspect of the present invention, the cover of the prosthetic foot is formed with a rear cavity located above and to the rear of the mounting flange of the keel. In addition, a larger primary cavity is formed in the foot cover at a location above the keel beam. These cavities further reduce the weight of the prosthetic foot.

BRIEF DESCRIPTION OF THE DRAWINGS

The details of typical embodiments of the present invention will be described in connection with the accompanying drawings, in which.

DETAILED DESCRIPTION OF THE PREFERRED EMBODIMENT

Figure 1:
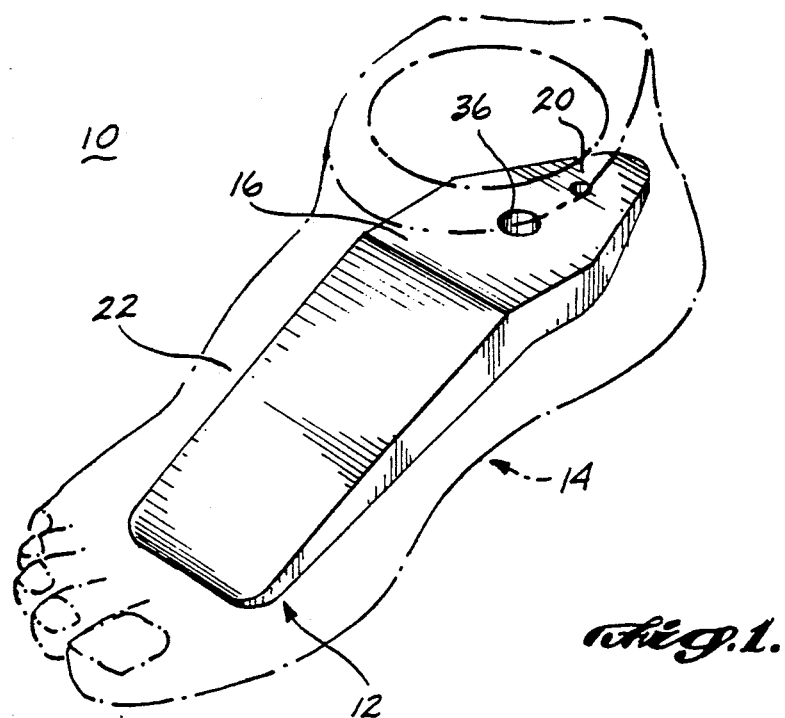
FIG. 1 is a front isometric view of a preferred embodiment of a prosthetic foot constructed in accordance with the present invention with a "low profile" cantilever spring keel wherein the cover or cosmesis is shown in broken line.
Figure 2:
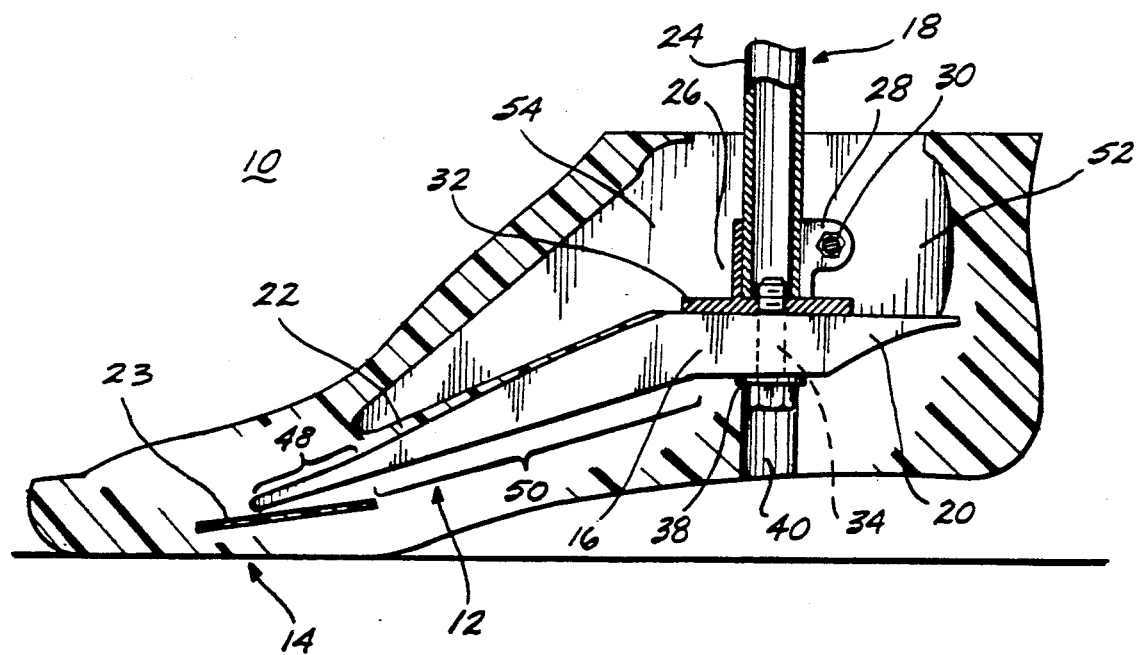
FIG. 2 is a side cross-sectional view of the prosthetic foot shown in FIG. 1, with the cover shown in solid line and with the addition of a fitting and hardware for attaching the prosthetic foot to a prosthetic pylon.
Figure 3:
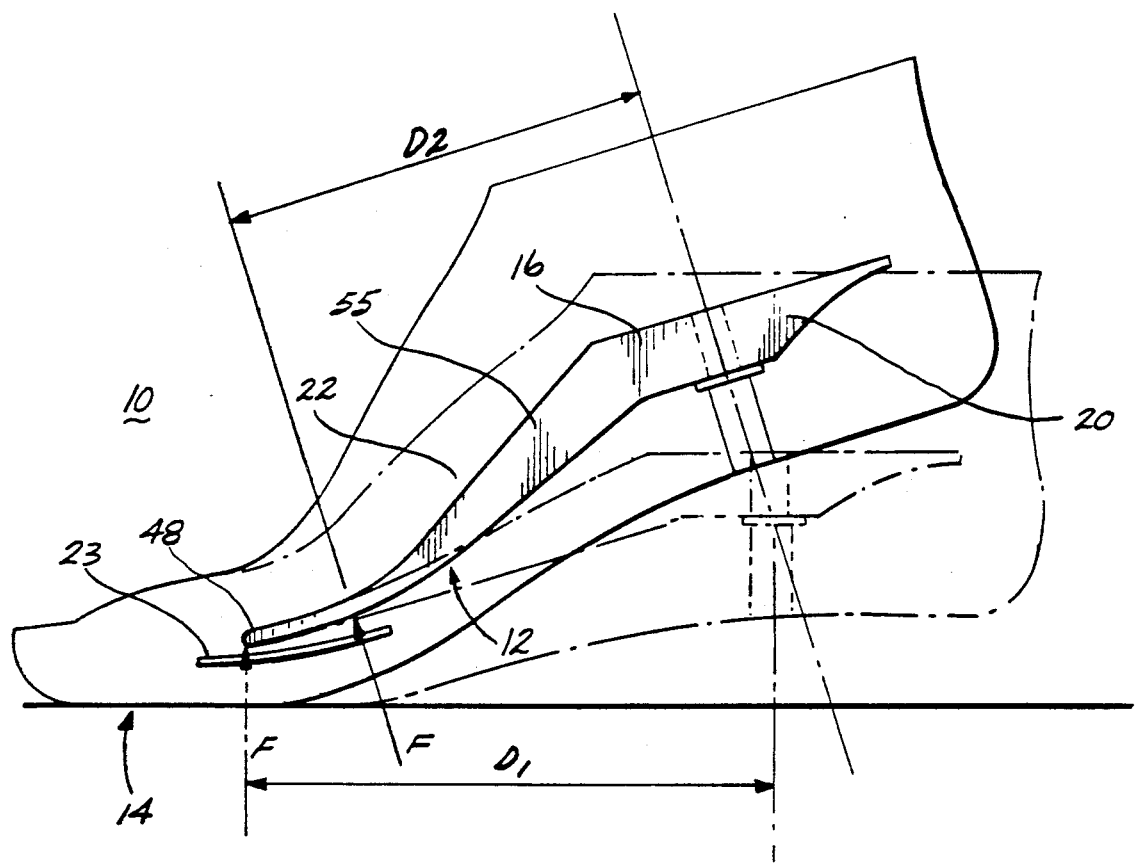
FIG. 3 is a side-elevational view of the prosthetic foot similar to FIG. 2 showing the location of the reaction loading on the prosthetic foot during footfall; and, FIG. 4 is a plan view of the cantilever spring keel utilized in the prosthetic foot of the present invention.

Referring initially to FIGS. 1-3, a prosthetic foot 10 includes a cantilever spring keel 12 formed from viscoelastic material and encased in a low-density, foamed polymer cover or cosmesis 14 molded to resemble the shape of a natural foot. The keel 12 includes a mounting or attachment flange 16 for attachment of the prosthetic foot to an upper prosthesis 18. The keel also includes a heel ledge 20 extending rearwardly from the mounting flange 16 and a singular, elongate forefoot portion or beam 22 cantilevered forwardly and downwardly from the mounting flange. A load-distributing toe plate 23 is located closely beneath the front tip of the beam 22.

The prosthetic foot 10 is designed to permit the wearer to ambulate with a substantially natural gait. To this end, during initial footfall, the heel portion of the cover disposed beneath the heel ledge 20 of the keel 12 is compressed to allow for a certain level of deflection of the cover. Thereafter, as the footfall continues, a reaction loading is applied to the beam 22 which flexes in a prescribed manner, initially relatively rapidly and then at a progressively slower rate to carry the weight of the amputee. During keel flexure, strain energy is stored therein and then subsequently released in a timed spring-back or restoration to impart an upward lift and forward thrust to the prosthetic foot.

Next, describing the construction and operation of the foregoing invention in greater detail, the keel mounting flange 16 is located longitudinally along the prosthetic foot 10 and elevationally low enough along the height of the prosthetic foot so that the foot is attachable to the upper prosthesis 18 at a location substantially corresponding to the location of the ankle joint. The flat top of the mounting flange, located relatively low within the cover 14, permits the prosthetic foot to be conveniently attached in a standard manner to the upper prosthesis 18 which includes a standard prosthetic pylon 24 extending downwardly through a relatively large cavity 52 formed in the cover 14 above the mounting flange and heel ledge. The bottom of the pylon is receivable within a standard industry fitting 26, illustrated as being of the split-collar clamping type. The fitting 26 includes a clamping portion 28 surrounding the bottom of the pylon 24 and tightly clamped thereto by a clamping bolt 30. The fitting 26 also includes a base portion 32 that overlies the top of the mounting flange 16 of the keel. An attachment bolt 34 extends upwardly through a close-fitting clearance bore 36 formed in the keel mounting flange 16 to engage with a corresponding threaded bore formed in fitting base 32. A flat washer 38 or similar hardware member is positioned between the head of the bolt 34 and the bottom surface of the keel mounting flange to distribute the compression load being applied to the keel mounting flange by the bolt 34. A through bore 40 is formed in the cover 14 beneath the mounting flange 16 to provide clearance for the head of the bolt 34 and the washer 38 and to provide access to these components.

It will be appreciated that, by locating the keel mounting flange 16 at a low elevation relative to the elevation of the keel forefoot beam 22, a smaller bending load is imposed on the attachment bolt 34 during use of the prosthetic foot 10, than would occur if the bolt were positioned at a higher elevation relative to the bottom of the prosthetic foot. As a result, the likelihood that the bolt 34 would fail from high bending loads or fatigue is reduced.

Figure 4:
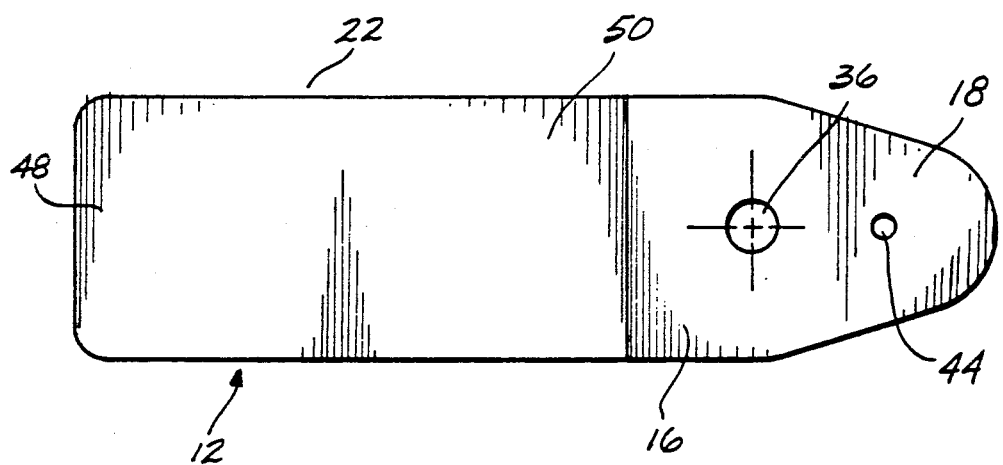

As shown most clearly in FIGS. 1 and 4, forwardly of the center of bore 36, the sides of mounting flange 16 are parallel and correspond to the sides of the keel beam 22. Rearwardly of the center of bore 34, the sides of mounting flange 16 taper to tangentially intersect the rounded rearward edge of the heel ledge 20. The tapered shape defined by the sides of the heel ledge, and the adjacent sides of the mounting flange, of course, is to accommodate the shape of the heel portion of the cover 14, which simulates the shape of the back of a natural foot. The heel ledge 20 provides an upper support or abutment for the heel portion of the cover, which is composed of resilient material that compresses during heel fall, i.e., as the bottom of the heel or the heel of the shoe, not shown, worn by the amputee, strikes the ground. It is to be understood that, in addition to utilizing resilient foamed polymer material, the other types of energy-restoring devices, such as compression springs, may be incorporated in the heel portion of the cover 14.

Additionally referring to FIGS. 2 and 3, the top surface of the heel ledge 20 preferably is coplanar with the top of the mounting flange 16, whereas the bottom of the heel ledge tapers upwardly in the rearward direction. Shaping the underside of the heel ledge in a tapered profile permits more of the resilient heel material of the cover to be placed beneath the ledge than would be possible if the underside of the ledge were not tapered in the rearward direction. Forming the heel ledge in this manner also reduces the weight of the prosthetic foot in that the material from which the keel is constructed, as discussed below, is substantially denser than the material from which the cover 14 is composed. In addition, it will be appreciated that the level of the bending stresses imposed on the heel ledge during heel fall decreases in the rearward direction, since the moment arm component of the bending stress imposed on the heel ledge decreases in this direction. This enables the thickness of the heel ledge to be decreased in the rearward direction without compromising the structural integrity of the heel ledge. The mounting flange 16 may include a bore 44 located rearwardly of the bore 36 for attachment of the keel 12 to an upper prosthesis utilizing a different type of connection device, not shown, than described above.

The forefoot beam 22 of the keel 12 cantilevers diagonally downwardly and forwardly from the mounting flange 16 to a location somewhat behind the forward tips of the toes formed in the cover 14. In plan view, the beam 22 is of constant width so that in transverse cross section, the beam is rectangular in shape. Although in construction the beam 22 is a singular member, it is composed of two sections: a rearward, primary section 50; and, a forward section 48. In accordance with one preferred embodiment of the present invention, the forward section 48 composes approximately one-quarter of the length of the beam 22, so that the primary section 50 composes approximately three-quarters of the length of the beam. Of course the relative lengths of the primary and forward sections may be altered in response to various factors, including, for example, the total length of the beam, the weight of the amputee, the maximum bending strength of the beam, the desired dynamic characteristics of the keel, etc. As described below, the two sections of the beam 22 have different structural and physical characteristics for desired load-carrying capacities, flexibility and other dynamic characteristics.

The primary section 50, as perhaps shown most clearly in FIGS. 2 and 3, is tapered in the forward direction, having a straight bottom surface and a parabolic-shaped top surface so that the capacity of the primary section to carry bending stresses is substantially constant along its length, but decreasing slightly in the forward direction. With this design parameter, if the keel were to fail, it is more likely that the failure would occur in the front portion of the primary section rather than rearwardly, toward the mounting flange. This is important in that the ability of the prosthetic foot to continue to function during failure decreases as the location of failure moves rearwardly along the keel length. The detrimental effect on the amputee of a keel failure is much less severe if it occurs toward the forward section rather than if failure occurs close to the mounting flange 16. The maximum thickness of the keel beam 22 is at its rearwardmost end, i.e., at its juncture with the mounting flange 16, and is sufficient to enable the keel to safely carry a load corresponding to approximately two and one-half times the body weight of the amputee.

The forward section 48 of the keel beam 22 is integrally constructed with and constitutes a continuation of the primary section 50. Relative to the primary section, the forward section is relatively thin and tapers slightly in the forward direction. Ideally, the bottom surface of the forward section is straight and coplanar with the bottom surface of the primary section 50. The top surface of the forward section 48 smoothly intersects with the top section of the adjacent portion of the primary section 50. In accordance with an illustrative but not limiting example of the present invention, the forward section 48 at its forward end may be of a thickness of approximately one-fifth the maximum thickness of the primary section 50, with the thickness of the forward section increasing slightly in the rearward direction to smoothly transition with the top of the primary section so as not to create a discontinuity in the keel beam 22. It will be appreciated that, by constructing the forward section 48 in the foregoing manner, the forward section exhibits significantly greater flexibility relative to the primary section when the beam 22 is initially loaded during footfall. The substantial compliance of the beam afforded by the forward section enables the prosthetic foot to closely simulate the "feel" of a natural foot. Moreover, by the foregoing construction, the structural integrity of the forward section 48 is sufficient to withstand the cyclical bending loads imposed thereon during each footfall.

By the foregoing construction of the keel 12 during footfall, the reaction force F from the ground is initially applied to the tip of the cantilevered beam 22, causing deflection thereof, with the deflection first occurring in the forward section 48, then progressively extending rearwardly to the primary section 50. As the deflection of the beam continues, the location at which the reaction force F is applied to the keel moves rearwardly along the beam, (see FIG. 3), eventually to a location ideally about one-third of the length of the beam rearwardly from the front tip thereof. It will be appreciated that, as the location at which the force F acts on the beam 22 moves rearwardly, the distance (designated as "D" in FIG. 3) between the location of such force and the mounting flange 16 decreases, resulting in a corresponding decrease in the moment arm and, thus, a reduction in bending stress created by the reaction force. As a result, the beam may be configured to define a smaller section modulus than would be required if the reaction force F on the beam remained at the front end thereof, rather than shifting rearwardly in the manner of the present invention. This enables the keel 12 to be constructed of a thickness that is thinner and/or of a width that is narrower than would otherwise be required to safely carry the weight of the amputee.

The shifting of the location of the reaction force F rearwardly along the beam 22 ideally occurs in a substantially continuous manner so that the beam is likewise flexed in a substantially continuous and gradual manner, thereby facilitating the ability of an amputee to achieve a natural gait through the use of the prosthetic foot 10. To this end, preferably, the bottom surface of the beam, including the primary section 50 and the forward section 48, is shaped to produce a straight taper, rather than a parabolic taper therealong as employed on the top surface of the beam. It will be appreciated that, if the top and bottom surfaces of the beam 22 were reversed from that shown in FIGS. 2 and 3, a discontinuity in the substantially continuous movement of the reaction force F rearwardly along the beam 22 would occur at the intersection of the forward section 48 and primary section 50 of the beam.

It will be appreciated that, as the location of application of the reaction force F moves rearwardly along the tapered beam 22, the spring rate of the keel 12 progressively increases. As an illustrative but not limiting example, for a keel having a beam approximately four inches long and approximately two inches wide, the spring rate of the keel may increase by a factor of approximately six from a range of approximately 100 lb/in to approximately 600 lb/in. By this increase in spring rate, the keel 12 of the present invention is capable of carrying a substantially greater load than would be possible if the spring rate did not increase in this manner but instead remained substantially constant. As a result, by constructing the keel 12 in the foregoing manner, maximum performance of the keel is achieved per unit weight of the keel while also enabling an amputee, wearing the prosthetic foot 10, to closely achieve a natural gait. As noted above, in prosthetic foot design, the minimization of weight is very important.

Moreover, by constructing the keel 12 as described above, the beam 22 need not extend forwardly to the furthermost portion of the cover 14. As such, it is possible to utilize the same keel 12 for several different cover sizes corresponding to at least three different foot sizes and to a relatively wide range of amputee weights, for example, a weight range of about fifty pounds. Further, by the foregoing construction, the size of the keel can be kept to a minimum, which contributes to the ability to position the mounting flange of the keel relatively low in the prosthetic foot, thereby allowing the prosthetic foot to be joined to an upper prosthesis at a location corresponding to the location of an ankle joint of a natural foot. As a consequence, the prosthetic foot 10 can be utilized by individuals who have had a Syme's amputation. Also, by positioning the keel mounting flange in this location, the prosthetic foot 10 can be joined to an upper prosthesis to be adjusted relative to each other in dorsal flexion and plantar flexion or with connection devices that simulate a natural ankle joint, not shown.

To enable the keel 12 to achieve the foregoing advantageous results, preferably, it is constructed from a hardened polymer or polymers capable of withstanding the large stresses placed on the keel and also the cyclical loading and unloading that occur during normal use, while still minimizing the weight of the keel. The hardened polymer material should have a moderate but not excessive flexural modulus to enable the keel to sufficiently deflect while withstanding high stress and cycling levels. In addition, the hardened polymer material used to form the keel should exhibit both elastic and viscous properties so that deflection and restoration of the keel under the cyclic loading of footfall and footrise produces a timed or lagging stress versus yield relationship, thereby to closely simulate the action of a natural foot. One particular type of hardened polymer material exhibiting the foregoing properties is acetal homopolymer, sold by DuPont Corporation under the trademark DELRIN. Acetal homopolymer exhibits a flexural modulus of approximately 380,000 psi and has the desired properties as discussed above.

In constructing the keel 12 of the present invention, it will be appreciated that reinforcing fibers can be utilized to strengthen the keel so that it can be formed from lighter weight polymers and/or formed in a smaller cross-sectional size. However, care must be taken not to counteract the viscous properties of the hardened polymer which provides the desired dampening effect. Examples of potentially useful high-strength fiber materials include carbon, aromatic polyamides (for examples, Kevlar from DuPont Corporation), and fiberglass.

Next describing the cover 14 in greater detail, preferably it is molded or otherwise shaped to resemble the form of a natural foot. Ideally, the cover is composed of a material capable of withstanding the many cycles of compression loading imparted on the heel strike during football and also the flexing of the keel beam. In addition, the cover material must be able to withstand surface abrasion resulting from the various types of footwear that the amputee may choose to wear. Also, importantly, the material from which the cover 14 is composed must be compatible with the polymer material used to form the keel 12. In this regard, the cover material must bond to the exterior surface of the keel so that shear loads acting at the interface of the keel and cover material are effectively transmitted therebetween. A preferred cover material meeting the foregoing requirements is a flexible, cellular polymer, for instance, polyurethane. Ideally, the material chosen and the production techniques utilized will result in a relatively low-density cover in the range of from about fifteen to twenty-five pounds per cubic foot.

As illustrated in FIGS. 2 and 3, the cover 14 is constructed with a rear void or cavity 52 located in the portion of the cover above the heel ledge 20 of the keel. A larger forward cavity 54 is located above the primary section 50 of the keel beam 22. The cavities 52 and 54 reduce the weight of the cover 14. It will be appreciated that constructing the keel 12 in the "low profile" described above and as illustrated in the drawings enables the cover 14 to be formed with the weight saving cavities 52 and 54. In many prior prosthetic feet, the keel occupies a substantially greater portion of the interior of the cover than occupied by keel 12 of the present invention. Applicant has found that, by constructing the keel 12 and the cover 14 in the manner described above, the weight of the prosthetic foot 10 is approximately one-half of the weight of a comparable size prosthetic foot constructed in accordance with the above-mentioned U.S. Pat. No. 4,645,509.

Still referring primarily to FIGS. 2 and 3, a thin, substantially flat and rigid toe plate 23 is embedded in the forward portion of the cover 14 closely below the forward tip of the keel beam 22. The toe plate 23 assists in distributing the downward load 48 imposed on the bottom of the cover by the forward section of the keel beam 22 about a substantial area of the bottom of the cover. This helps prevent the cover from failing or otherwise being damaged by the shear stresses and other stresses imposed thereon by the keel beam, especially when the keel beam is flexed during footfall. Preferably, the toe plate 23 is constructed from high strength but lightweight material(s). As an illustrative but nonlimiting example, the toe plate 23 may be composed of urethane reinforced by polyethylene fibers, for instance, Compet fibers from Allied Chemicals.

As will be apparent to those skilled in the art, the present invention may be embodied in forms other than those specifically disclosed above without departing from the spirit or essential characteristics of the invention. The particular embodiment of the prosthetic foot 10, described above, is therefore to be considered in all respects as being merely illustrative of a prosthetic foot capable of carrying out the present invention. The scope of the present invention is as set forth in the following claims, rather than being limited to the foregoing description.

The embodiments of the invention in which an exclusive property or privilege is claimed are defined as follows:

1. A prosthetic foot, comprising:
   (a) a cantilever spring keel having viscoelastic properties;
   (b) a cover encasing the keel, the cover having an exterior shape generally resembling a human foot; and,
   (c) wherein the keel having:
      (i) an attachment portion for connecting the keel to an upper prosthesis at a longitudinal location along the length of the prosthetic foot and at an elevation along the height of the prosthetic foot approximating the elevation of the ankle joint of a human foot, the attachment portion having a forward section and a rearward section; and,
      (ii) a monolithic forefoot portion cantilevered extending forwardly and diagonally downwardly from the forward section of the attachment portion to the front end of the keel and at least approaching a point within the cover corresponding to the toes of a human foot, said forefoot portion being shaped and dimensioned to flex upwardly and thereby store strain energy during footfall and then with the following footrise, release such strain energy as foot lift and thrust as the forefoot portion regains its nominal configuration, with the location of the upward reaction force being applied to the keel during footfall progressively and continuously moving backward along the forefoot portion from the front of the keel so as to progressively decrease the effective beam length and progressively increase the spring rate of the keel.

2. The prosthetic foot according to claim 1, wherein the location that the reaction force is applied to the forefoot portion moves rearwardly along the forefoot portion approximately one-third of the length of the forefoot portion during footfall.

3. The prosthetic foot according to claim 1, wherein the forefoot portion of the keel is shaped to impart a progressively lower bending stress level on the keel along the forefoot portion in the direction toward the attachment portion during flexure of the keel during footfall.

4. The prosthetic foot according to claim 1, further comprising a heel ledge extending from the attachment portion of the keel in the direction opposite to the forefoot portion.

5. The prosthetic foot according to claim 4, wherein the heel ledge is tapered in the direction away from the attachment portion of the keel.

6. The prosthetic foot according to claim 1, wherein the cover includes a rear cavity located above and to the rear of the mounting portion of the keel.

7. A prosthetic foot comprising:
   (a) a cantilever spring keel having viscoelastic properties;
   (b) a cover encasing the keel, the cover having an exterior shape generally resembling a human foot;
   (c) wherein the keel having:
      (i) an attachment portion for connecting the keel to an upper prosthesis at a longitudinal location along the length of the prosthetic foot and at an elevation along the height of the prosthetic foot approximating the elevation of the ankle joint of a human foot, the attachment portion having a forward section and a rearward section;
      (ii) monolithic forefoot portion cantilevered forwardly and diagonally downwardly from the forward section of the attachment portion, said forefoot portion being shaped and dimensioned to flex upwardly and thereby store strain energy during footfall and then with the following footrise, release such strain energy as foot lift and thrust as the forefoot portion regains its nominal configuration, with location of the upward reaction force being applied to the keel during footfall progressively moving backward along the forefoot portion from the front of the forefoot portion so as to progressively decrease the effective beam length and progressively increase the spring rate of the keel;
   (d) the forefoot portion of the keel has a forward section and a primary section extending between the forward section and the forward section of the attachment portion of the keel; and,
   (e) the forward section of the forefoot portion has a significantly lower spring rate than the adjacent portions of the primary section of the forefoot portion of the keel to facilitate deflection and compliance of the forward section during footfall.

8. The prosthetic foot according to claim 7, wherein the spring rate of the forward section of the forefoot portion of the keel increases in the direction toward the attachment portion of the keel at a significantly lower rate than the rate of increase of the spring rate of the primary section of the forefoot portion of the keel in the direction toward the attachment portion of the keel.

9. The prosthetic foot according to claim 7, wherein the primary section of the forefoot portion of the keel has a thickness that varies as a parabolic taper.

10. The prosthetic foot according to claim 9, wherein the primary section of the forefoot portion of the keel has a generally planar lower surface and an upper surface having a profile along the length of the primary section to form the thickness of the primary section as a parabolic taper.

11. The prosthetic foot according to claim 9, wherein the parabolic taper of the primary section of the keel forefoot portion is shaped to impart on the primary section progressively lower bending stress levels in the direction from the tip section to the attachment portion of the keel.

12. A prosthetic foot, comprising:
   (a) a cantilever spring keel having viscoelastic properties;
   (b) a cover encasing the keel, the cover having an exterior shape generally resembling a human foot;
   (c) wherein the keel having:
      (i) an attachment portion for connecting the keel to an upper prosthesis at a longitudinal location along the length of the prosthetic foot and at an elevation along the height of the prosthetic foot approximating the elevation of the ankle joint of a human foot, the attachment portion having a forward section and a rearward section;
      (ii) monolithic forefoot portion cantilevered forwardly and diagonally downwardly from the forward section of the attachment portion, said forefoot portion being shaped and dimensioned to flex upwardly and thereby store strain energy during footfall and then with the following footrise, release such strain energy as foot lift and thrust as the forefoot portion regains its nominal configuration, with the location of the upward reaction force being applied to the keel during footfall progressively moving backward along the forefoot portion from the front of the forefoot portion so as to progressively decrease the effective beam length and progressively increase the spring rate of the keel; and, (d) a heel ledge extending from the mounting portion of the keel in the direction opposite to the forefoot portion, the heel ledge including a top surface and a bottom surface sloped upwardly toward the top surface in the direction extending away from the mounting portion of the keel.

13. A prosthetic foot, comprising:
(a) a cantilever spring keel having viscoelastic properties;
(b) a cover encasing the keel, the cover having an exterior shape generally resembling a human foot;
(c) wherein the keel having:
  (i) an attachment portion for connecting the keel to an upper prosthesis at a longitudinal location along the length of the prosthetic foot and at an elevation along the height of the prosthetic foot generally corresponding to the location of the ankle joint of a human foot; and,
  (ii) a forefoot portion cantilevered forwardly and diagonally downwardly from the attachment portion, said forefoot portion being shaped and dimensioned to flex upwardly and thereby store strain energy during footfall and then with the following footrise, release such strain energy as foot lift and thrust as the forefoot portion regains its nominal configuration, with the location of the upward reaction force being applied to the keel during footfall progressively moving backward along the forefoot portion from the front of the forefoot portion so as to progressively decrease the effective beam length and progressively increase the spring rate of the keel;
(d) comprising a heel ledge extending from the mounting portion of the keel in the direction opposite to the forefoot portion, the heel ledge including a top surface, and a bottom surface sloped upwardly toward the top surface in the direction extending away from the mounting portion of the keel; and,
(e) wherein the attachment portion of the keel has a substantially planar upper surface, and the top surface of the heel ledge is substantially coplanar with the upper surface of the attachment portion.

14. A prosthetic foot comprising:
(a) a cantilever spring keel having viscoelastic properties;
(b) a cover encasing the keel, the cover having an exterior shape generally resembling a human foot;
(c) wherein the keel having:
  (i) an attachment portion for connecting the keel to an upper prosthesis at a longitudinal location along the length of the prosthetic foot and at an elevation along the height of the prosthetic foot approximating the elevation of the ankle joint of a human foot, the attachment portion having a forward section and a rearward section;
  (ii) monolithic forefoot portion cantilevered extending forwardly and diagonally downwardly from the forward section of the attachment portion and at least approaching a point within the cover corresponding to the toes of a human foot, said forefoot portion being shaped and dimensioned to flex upwardly and thereby store strain energy during footfall and then with the following footrise, release such strain energy as foot lift and thrust as the forefoot portion regains its nominal configuration, with the location of the upward reaction force being applied to the keel during footfall progressively moving backward along the forefoot portion from the front of the forefoot portion so as to progressively decrease the effective beam length and progressively increase the spring rate of the keel; and,
(d) the cover includes a major cavity located above the forefoot portion of the keel and extending from the mounting portion of the keel forwardly a substantial distance toward the forward end of the forefoot portion.

15. A prosthetic foot, comprising:
(a) a cantilever spring keel having viscoelastic properties;
(b) a cover encasing the keel, the cover having an exterior shape generally resembling a human foot;
(c) wherein the keel having:
  (i) an attachment portion for connecting the keel to an upper prosthesis at a longitudinal location along the length of the prosthetic foot and at an elevation along the height of the prosthetic foot approximating the elevation of the ankle joint of a human foot, the attachment portion having a forward section and a rearward section;
  (ii) monolithic forefoot portion cantilevered forwardly and diagonally downwardly from the forward section of the attachment portion, said forefoot portion being shaped and dimensioned to flex upwardly and thereby store strain energy during footfall and then with the following footrise, release such strain energy as foot lift and thrust as the forefoot portion regains its nominal configuration, with the location of the upward reaction force being applied to the keel during footfall progressively moving backward along the forefoot portion from the front of the forefoot portion so as to progressively decrease the effective beam length and progressively increase the spring rate of the keel; and,
(d) a thin, substantially rigid toe plate disposed beneath the free end of the forefoot portion of the keel to assist in distributing the load imposed on the bottom of the cover by the keel forefoot portion.

16. A keel for a prosthetic foot, comprising a cantilever spring member exhibiting viscoelastic properties, said cantilever spring member including:
(a) a mounting portion for connecting the keel to an upper prosthesis at a location approximating the location of the ankle joint of a human foot, the mounting portion having a forward section and a rearward section; and,
(b) a monolithic forefoot beam cantilevered extending forwardly and diagonally downwardly from the forward section of the mounting portion to the front end of the keel and at least approaching a point of the prosthetic foot corresponding the toes of a human foot, said beam being shaped and dimensioned to flex upwardly and thereby store strain energy during footfall and then with the following footrise, releasing such strain energy in the form of foot lift and thrust as the beam returns to its nominal configuration, with the location of the upward reaction force being applied to the beam during footfall progressively and continuously shifting rearward along the keel from the front of the keel to progressively decrease the distance between the location of the upward reaction force and the mounting portion and progressively increase the spring rate of the keel.

17. The keel for a prosthetic foot according to claim 16, wherein the location that the reaction force is applied to the beam during footfall moves rearwardly along the beam approximately one-third of the length of the beam during footfall.

18. The keel for a prosthetic foot according to claim 16, wherein the cantilevered beam of the keel is shaped to impart a progressively lower bending stress level along the beam in the direction toward the mounting portion during flexure of the keel during footfall.

19. The keel for a prosthetic foot according to claim 16, further comprising a heel ledge extending from the mounting portion of the keel in the direction opposite to the beam.

20. The keel for a prosthetic foot according to claim 19, wherein the heel ledge is tapered in the direction away from the mounting portion of the keel.

21. A keel for a prosthetic foot, comprising a cantilever spring member exhibiting viscoelastic properties, said cantilever spring member including:
   (a) a mounting portion for connecting the keel to an upper prosthesis at a location approximating the location of the ankle joint of a human foot, the mounting portion having a forward section and a rearward section;
   (b) a singular forefoot beam cantilevered forwardly and diagonally downwardly from the forward section of the mounting portion, said beam being shaped and dimensioned to flex upwardly and thereby store strain energy during footfall and then with the following footrise, releasing such strain energy in the form of foot lift and thrust as the beam returns to its nominal configuration, with the location of the upward reaction force being applied to the beam during footfall progressively shifting rearward along the beam from the front of the beam to progressively decrease the distance between the location of the upward reaction force and the mounting portion and progressively increase the spring rate of the keel;
   (c) the beam of the keel having a forward section and a primary section extending between the forward section and the forward section of the mounting portion of the keel; and,
   (d) the forward section of the beam having an appreciably lower spring rate than adjacent portions of the primary section of the beam.

22. A keel for a prosthetic foot comprising a cantilever spring member exhibiting viscoelastic properties, said cantilever spring member including:
   (a) a mounting portion for connecting the keel to an upper prosthesis at a location approximating the location of the ankle joint of a human foot, the mounting portion having a forward section and a rearward section;
   (b) a singular forefoot beam cantilevered forwardly and diagonally downwardly from the forward section of the mounting portion, said beam being shaped and dimensioned to flex upwardly and thereby store strain energy during footfall and then with the following footrise, releasing such strain energy in the form of foot lift and thrust as the beam returns to its nominal configuration, with the location of the upward reaction force being applied to the beam during footfall progressively shifting rearward along the beam from the front of the beam to progressively decrease the distance between the location of the upward reaction force and the mounting portion and progressively increase the spring rate of the keel;
   (c) the beam of the keel having a forward section and a primary section extending between the forward section and the forward section of the mounting portion of the keel;
   (d) the forward section of the beam having an appreciably lower spring rate than adjacent portions of the primary section of the beam; and,
   (e) wherein the spring rate of the forward section of the beam increases in the direction toward the mounting portion of the keel at a significantly lower rate than the rate of increase of the spring rate of the primary section of the beam in the direction toward the mounting portion of the keel.

23. A keel for a prosthetic foot, comprising a cantilever spring member exhibiting viscoelastic properties, said cantilever spring member including:
   (a) a mounting portion for connecting the keel to an upper prosthesis at a location approximating the location of the ankle joint of a human foot the mounting portion having a forward section and a rearward section;
   (b) a singular forefoot beam cantilevered forwardly and diagonally downwardly from the forward section of the mounting portion, said beam being shaped and dimensioned to flex upwardly and thereby store strain energy during footfall and then with the following footrise, releasing such strain energy in the form of foot lift and thrust as the beam returns to its nominal configuration, with the location of the upward reaction force being applied to the beam during footfall progressively shifting rearward along the beam from the front of the beam to progressively decrease the distance between the location of the upward reaction force and the mounting portion and progressively increase the spring rate of the keel;
   (c) the beam of the keel has a forward section and a primary section extending between the forward section and the forward section of the mounting portion of the keel;
   (d) the forward section of the beam has an appreciably lower spring rate than the adjacent portions of the primary section of the beam; and,
   (e) wherein the primary section of the beam having a thickness that varies as a parabolic taper.

24. The keel for a prosthetic foot according to claim 23, wherein the primary section of the beam has a generally planar lower surface and an upper surface having a longitudinal profile to form the thickness of the primary section as a parabolic taper.

25. The keel for a prosthetic foot according to claim 23, wherein the parabolic taper of the primary section of the keel beam is shaped to impart progressively lower bending stress levels on the primary section in the direction from the forward section to the mounting portion of the keel.

26. A keel for prosthetic foot comprising a cantilever spring member exhibiting viscoelastic properties, said cantilever spring member including:
(a) a mounting portion for connecting the keel to an upper prosthesis at a location approximating the location of the ankle joint of a human foot the mounting portion having a forward section and a rearward section; and
(b) a singular forefoot beam cantilevered forwardly and diagonally downwardly from the forward section of the mounting portion, said beam being shaped and dimensioned to flex upwardly and thereby store strain energy during footfall and then with the following footrise, releasing such strain energy in the form of foot lift and thrust as the beam returns to its nominal configuration, with the location of the upward reaction force being applied to the beam during footfall progressively shifting rearward along the beam from the front of the beam to progressively decrease the distance between the location of the upward reaction force and the mounting portion and progressively increase the spring rate of the keel; and,
(c) a heel ledge extending from the attachment portion of the keel in the direction opposite to the beam, the heel ledge includes a top surface and a bottom surface sloped upwardly toward the top surface in the direction extending away from the mounting portion of the keel.

* * * * *

UNITED STATES PATENT AND TRADEMARK OFFICE
CERTIFICATE OF CORRECTION

PATENT NO. : 5,066,305

DATED : November 19, 1991

INVENTOR(S) : D.G. Firth

It is certified that error appears in the above-identified patent and that said Letters Patent is hereby corrected as shown below:

| COLUMN | LINE | ERROR |
|---|---|---|
| 7 | 33 | after "prosthesis" insert --with connection devices that enable the prosthetic foot and the upper prosthesis--. |
| 8 | 6 | "football" should be --footfall--. |

Signed and Sealed this

Sixteenth Day of March, 1993

*Attest:*

STEPHEN G. KUNIN

*Attesting Officer*   *Acting Commissioner of Patents and Trademarks*